United States Patent [19]
Plummer

[11] 4,018,514
[45] Apr. 19, 1977

[54] APPARATUS FOR RETINAL PHOTOGRAPHY
[75] Inventor: William T. Plummer, Concord, Mass.
[73] Assignee: Polaroid Corporation, Cambridge, Mass.
[22] Filed: Sept. 25, 1975
[21] Appl. No.: 616,599
[52] U.S. Cl. .................................... 351/7; 351/38
[51] Int. Cl.² .......................................... A61B 3/14
[58] Field of Search ..................... 351/6, 7, 30, 38

[56] References Cited
UNITED STATES PATENTS

| | | | |
|---|---|---|---|
| 3,016,000 | 1/1962 | Noyori | 351/7 |
| 3,236,578 | 2/1966 | Mackworth | 351/7 |
| 3,315,680 | 4/1967 | Silbertrust et al. | 351/6 |
| 3,698,099 | 10/1972 | Matsura | 351/7 |

Primary Examiner—Harold A. Dixon
Attorney, Agent, or Firm—John W. Ericson; John S. Vale

[57] ABSTRACT

Apparatus for retinal photography comprising an energy supply unit, a hand lens, a foot-operated control unit, and headgear comprising an indirect ophthalmoscope combined with a camera and mounted on a helmet adapted to be worn by the photographer. The headgear is partially suspended from an overhead support by a negator spring and a cable suspension permitting universal movement. Light for examining the retina, and a bright flash of light for photography, are supplied to the headgear over a flexible fiber optics cable under the control of the foot-operated unit and synchronizing contacts on the camera.

9 Claims, 8 Drawing Figures

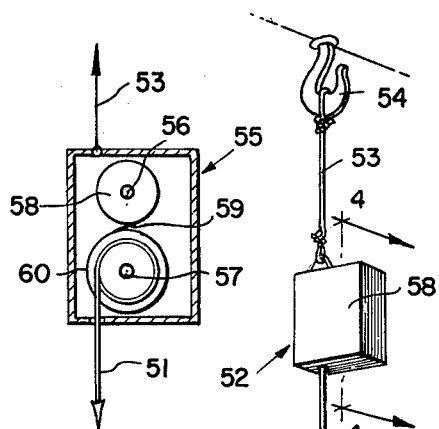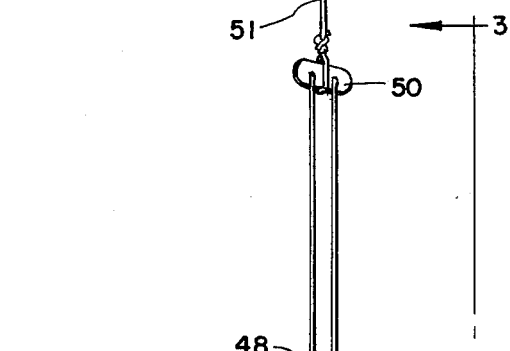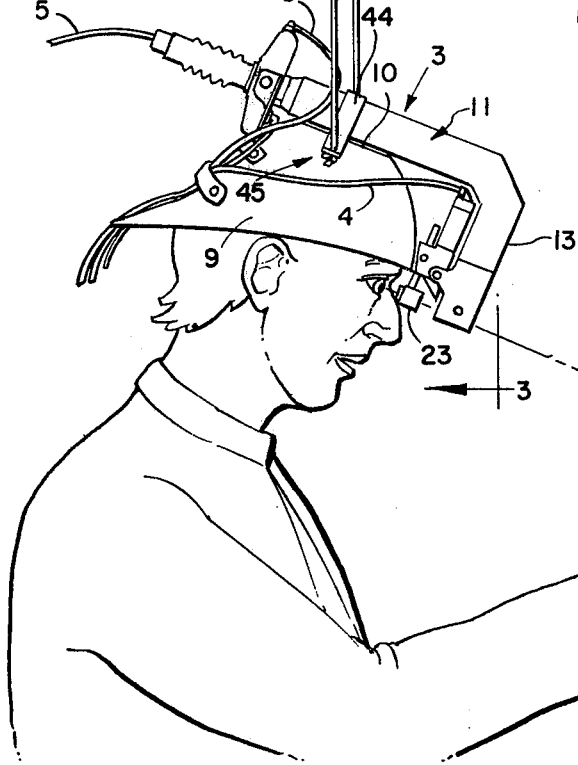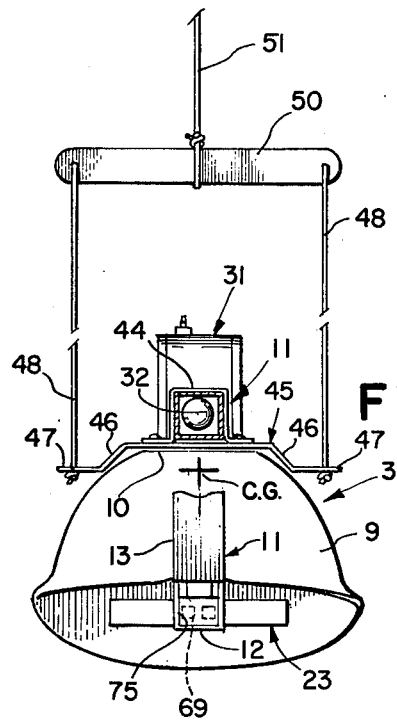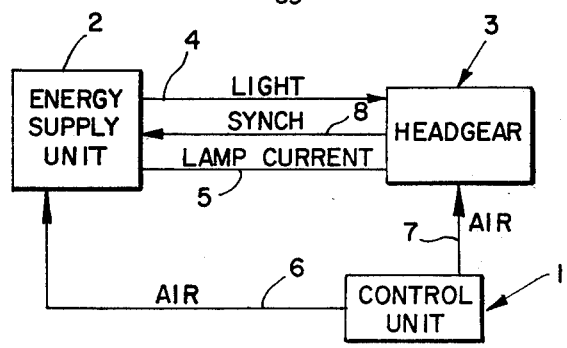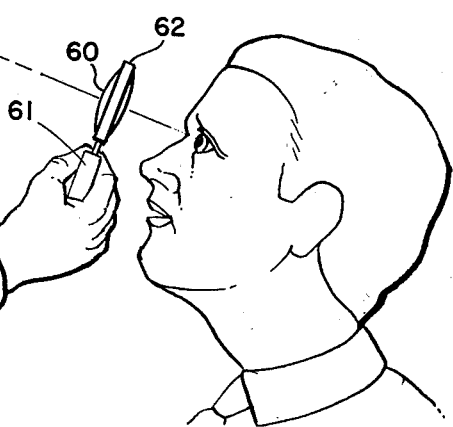

APPARATUS FOR RETINAL PHOTOGRAPHY

This invention relates to photography, and particularly to novel apparatus for photographing the retina of the eye.

Photographs of the retina are of great value in many fields of medicine and science, and in particular to the ophthalmologist. Many forms of cameras for photographing the eye have been developed to meet the demand for such photographs.

One group of retinal cameras is described in "Retinal Camera Review", an article by Peter Hansell of the Institute of Ophthalmology in London, England, and published in 1957 in Medical and Biological Illustration, Vol. 7, on pages 91–97. The cameras described in this article are basically bulky stand models, with an adjustable head rest for the patient.

A combined single lens reflex camera and ophthalmoscope is described in "Retinal Photography and Ophthalmoscopy Combined in One Instrument", by Geraldo Queiroga of Belo Horizonte, Brazil, published in the American Journal of Ophthalmology in 1969, Vol. 49, pages 1403–1406. The combined instrument is also stand-mounted.

The physician-photographer commonly encounters considerable difficulty in manipulating the patient with a stand camera so that the desired region can be photographed. One root of this difficulty is the fact that, as a photographer, the operator must manipulate the patient using different movements and techniques than he would as a physician examining the eye.

One form of apparatus that has been devised as a solution to this problem is described in the December 1964 issue of The Archives of Ophthalmology, Vol. 72, pages 788–791, in an article by William J. Stenstrom entitled "Cinematography of the Human Fundus". The apparatus there described comprises a movie camera combined with an indirect ophthalmoscope in a portable unit adapted to be suspended from the chest of the photographer-physician, and used together with a hand-held lens to examine and photograph the eye while allowing the examiner some freedom to manipulate the patient. The combined apparatus is rather heavy and bulky, and may be quite fatiguing to the user.

In an article published on pages 81–89 of Vol. 17, the 1967 edition of Medical and Biological Illustration, entitled "Retinal Camera Review-II" by Peter Hansell, four additional bench or floor standing retinal cameras, and three hand-held cameras, are described. The hand-held cameras all require an approach to the corneal surface of between 4 to 8 mm, and thus inhibit some of the usual manipulative procedures employed by the examiner. A method of fundus photography which goes even farther in this direction, for the purpose of obtaining a wide field of view, is described in Investigative Ophthalmology, Vol. 14, pages 401–406, in an article entitled "Equator-Plus Camera" by Oleg Pomerantzeff. The camera there described requires actual contact with the patient's eye.

The object of this invention is to make it possible for a physician to conveniently photograph the retina of a patient while examining the patient's eye in the manner, and with the manipulative techniques, to which he has been trained.

Briefly, the above and other objects of the invention are attained by the construction of a novel combination of camera and indirect ophthalmoscope in which many of the elements that normally contribute weight to such apparatus are mounted in a separate energy supply unit that can be placed on the floor or on a table near the examining physician. An objective lens is provided that is held in one hand by the examiner in front of the patient's eye to form an aerial image of the retina.

The remaining elements of the combined camera and ophthalmoscope are mounted on a helmet to be worn on the head of the user. This headgear is partially suspended from the ceiling by a suspension which includes a negator spring to reduce the weight of the apparatus, as felt by the user, to a small value, such as one pound. The suspension further comprises a universal cable assembly that allows the user freedom to move his head in any manner convenient for the examination of the patient's eye.

A foot-operated control unit is provided which controls the apparatus in a manner to be described to make a photograph at the will of the operator. Light is supplied from the energy supply unit to the headgear over a flexible fiber optics cable. A camera shutter is actuated by a pneumatic actuator under the control of the foot unit. The camera's synchronizing contacts are connected to the energy supply unit over an electrical cable, and cause the discharge of an electronic flash unit in the energy supply unit at a time when the shutter is open. Another electrical cable from the headgear to the energy supply unit conveys electrical current to operate an illuminator lamp for focusing purposes in a manner to be described.

Just before the shutter is tripped by the foot control unit, a light switch in the energy supply unit is actuated by the foot unit and causes the fiber optics cable connected to the headgear to be switched from a position in which it receives light from an illuminating lamp used for examination purposes, to a position in which it receives light from the electronic flash unit when the unit is discharged. The photographer examines the retina through an optical path including a binocular pair of periscopes which view the retina through a beam splitting mirror in the headgear, and through the hand-held lens described above. The major portion of the light falling on the beam splitter from the image of the patient's retina formed by the hand lens is reflected from the beam splitter to the camera, where it is used to make a photograph.

At times when a photograph is not being made, a mirror in the camera directs light from the camera's focusing screen into the retina. The focusing screen is illuminated for this purpose by a lamp in an illuminator mounted on the camera. The camera is focused by the examiner viewing the image of a central region of the illuminated focusing screen of the camera, on which cross hairs, microprisms, or the like may be placed, superimposed on the image of the retina. The examiner is free to manipulate the patient's eye in any conventional manner during the process of examination and photography.

The manner in which the apparatus of the invention is constructed, and its mode of operation, will best be understood in the light of the following detailed description, together with the accompanying drawings, of a preferred embodiment thereof.

In the drawings,

FIG. 1 is a schematic block diagram generally illustrating the structural and functional relationships between the headgear, energy supply unit and control unit of the apparatus of the invention;

FIG. 2 is a schematic fragmentary elevational sketch illustrating the headgear and its suspension in use by an examiner, in combination with a hand-held lens, to examine and photograph the retina of a subject;

FIG. 3 is a fragmentary schematic exploded sketch of a portion of the apparatus of FIG. 2, taken substantially along the lines 3—3 in FIG. 2, with parts shown in cross section and parts broken away;

FIG. 4 is a diagrammatic elevational sketch, on an enlarged scale, of a negator spring forming a part of the apparatus of FIG. 2;

Figure 5:
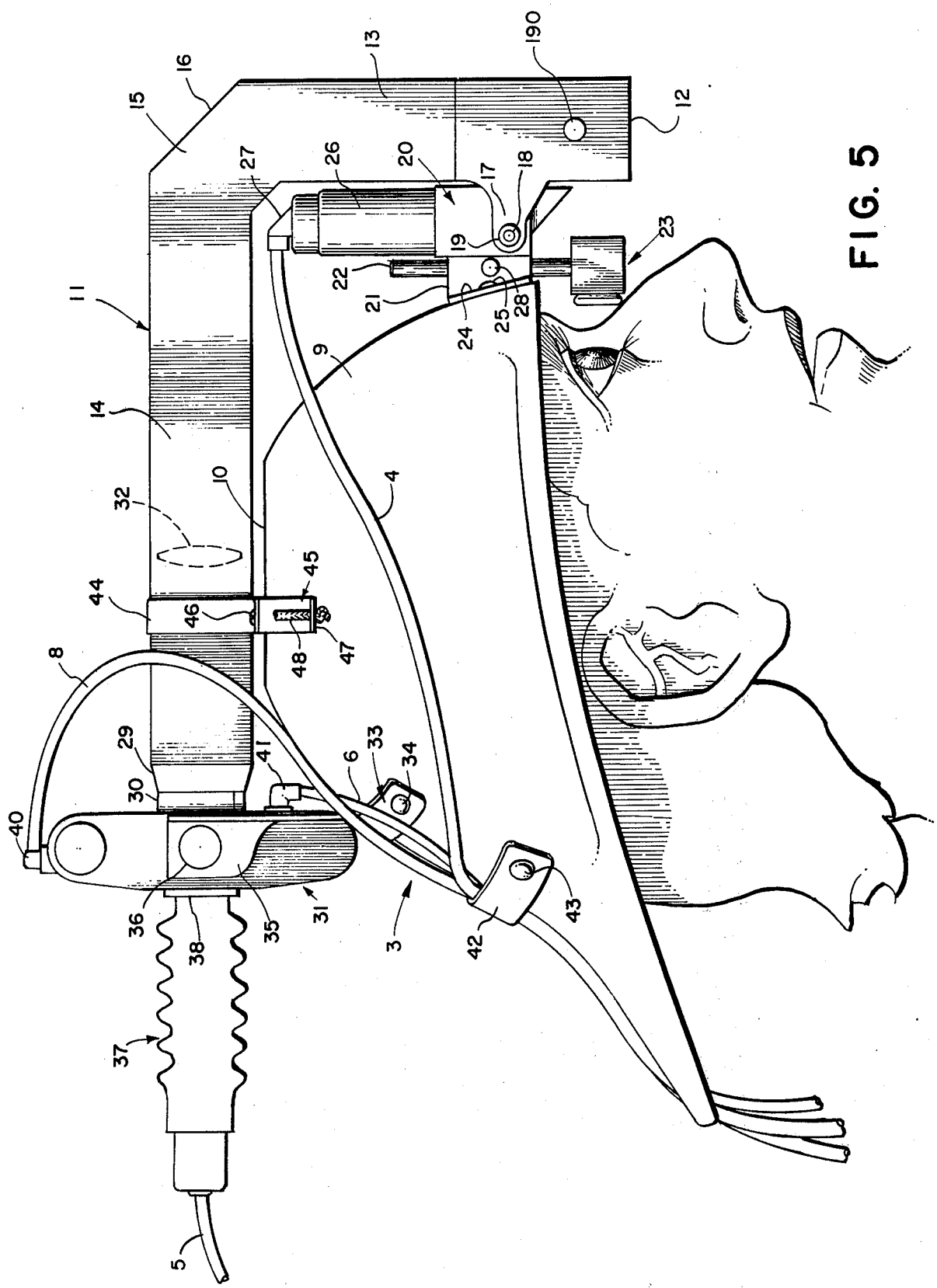
FIG. 5 is an elevational sketch, on an enlarged scale, of a portion of the apparatus of FIG. 2.

FIG. 1 shows the structural and functional relationships between a foot-operated control unit 1, an energy supply unit diagramatically shown at 2, and headgear schematically indicated at 3. As will be described in more detail below, when the control unit 1 is not operated, the headgear functions in an examination mode, receiving illuminating light from a projection lamp in the energy supply unit 2 over a flexible fiber optics cable 4. Electrical current for operating a focusing lamp in the headgear 3 is supplied over wires diagramatically indicated at 5.

The control unit 1 is connected to the energy supply unit 2 over a hose 6 that at times supplies a pulse of air under pressure to a pneumatic actuator in the energy supply unit, to be described. A similar air hose 7 is connected between the control unit 1 and the headgear 3, to actuate a pneumatic shutter actuator when the control unit is operated. As will appear, when the operator presses his foot on the control unit 1, a pulse of air is first supplied through the hose 6 to change the cable connections for the light conducting cable 4 to communication with an electronic flash unit. A pulse of air is then sent over the hose 7 to actuate the shutter, whereupon a synchronizing signal is supplied from the synchronizing contacts of the camera, to be described, to actuate the flash unit in the energy supply unit 2 and supply a pulse of light over the cable 4 for photography.

FIGS. 2 and 3 show the headgear 3 and its overhead partial suspension system, next to be described. As shown, the headgear 3 comprises a helmet 9, which may be a conventional hard hat of the type worn by miners or the like, with the top cut off as indicated at 10, to provide clearance from optical housing 11.

The housing 11 may be formed of sheet metal or the like, and forms a generally L-shaped channel of rectangular cross section. Comparing FIGS. 3 and 5, the channel 11 extends from a closed end 12 through a vertical section 13 that is joined to a normally horizontal section 14 through an inclined section 15, providing with a wall 16 at 45° to the sections 14 and 13, respectively, behind which a mirror is located for purposes to be described.

A bracket 17 formed integral with the rising section 13 is journalled on a shaft 18 that also serves as a mirror support, in a manner to be described. A knob 19 fixed on the shaft 18 is provided for adjusting the angle of the mirror for purposes to be described below. The shaft 18 is rotatably supported in suitable bores formed in a bracket 20.

The bracket 20 has an integral arm portion 21 bored to slidably receive a shaft 22. The shaft 22 is fixed to a binocular periscope generally designated 23 and to be described in more detail below. The shaft 22 is adjustably secured in the arm 21 by means of a thumb screw 28, whereby the periscope 22 can be raised and lowered to suit the operator's eye level. A mounting bracket 24 is formed integral with the arm 21, and is secured to the helmet 9 by any suitable conventional means, indicated as rivets 25.

Fixed in the bracket 20 is the housing 26 of a conventional ophthalmoscopic illuminator, to be described in more detail below. The illuminator 26 receives light from the fiber optics cable 4 through an intermediate prism 27 connected to the top of the housing 26. The cable 4 may be a conventional bundle of fine glass fibers sheathed in an opaque plastic outer cover.

The illuminator in the housing 26, the cable 4 and the periscope 23 form parts of a conventional indirect ophthalmoscope, which is normally secured to the head of the user by a headband. It has been found that it is much more convenient to support on the helmet 9, as this is considerably less fatiguing to the user. The prism 27 is inserted between the cable 4 and the illuminator housing to direct the cable back along the helmet 9 at a convenient angle.

An indirect ophthalmoscope is an optical instrument that is used to observe an aerial image of the retina provided by an auxiliary lens that is generally hand held in front of the patient's eye. A direct opthalmoscope, on the other hand, is used to observe the retina directly.

The housing 11 terminates at the end of the portion 14 in a region 29 which converges aid is formed integral with a cylindrical section 30 formed in any conventional manner, not shown, as an adapter to secure it to the lens mount of a conventional camera 31, here shown as a conventional single lens reflex camera for 35 mm film. A long focus objective lens for the camera 31 is mounted in the housing section 14 as suggested at 32, in an optical arrangement to be described below.

The camera 31 is mounted on the helmet 9 by means of an intermediate bracket 33 secured to the helmet in any conventional manner, as suggested by rivets 34. The upper end 35 of the bracket 33 is formed as a flange that is secured to the tripod socket of the camera through an intermediate hand screw 36.

A focus illuminator generally designated 37 is formed with a flange 38 for attachment to the camera, so that the illuminator provides light to the camera's viewfinder in a manner to be described below. Electrical energy for a lamp in the illuminator 37 is provided over the cable 5 as described above.

The synchronizing cable 8 is connected by a conventional connector suggested at 40 to the synchronizing contacts of the camera. The air hose 6 is connected to the camera shutter through an intermediate pneumatic actuator 41.

The electrical, pneumatic and optical cables 8, 6 and 4 are collected together at the rear of the helmet 9 and there held by a suitable bracket 42, riveted or otherwise secured to the helmet 9 as indicated at 43. The bracket 42 holds the cable assemblage out of the way of the operator.

It will be apparent that the photographic apparatus just described, comprising the housing 11, camera 31 and illuminator 37 is firmly secured to the helmet 9 at two points; by the shaft 18 and the bracket 17, and by the bracket 33. The housing 11 serves as a support for the entire headgear.

For this purpose, a bracket 44, of metal or the like, secures the housing 11 to a bracket 45, as with machine screws 46 shown in FIG. 5. The bracket 45 has arms bent downwardly as suggested at 46 that are bent again to form horizontal ends 47 formed with apertures for connection to a pair of supporting flexible cables 48. The connections to the cables 48 are located along an axis passing through the center of gravity CG of the headgear, as indicated by the cross in FIG. 3. As shown in FIGS, 2 and 3, the cables 48 are connected at their upper ends to the ends of a rigid bar 50, of sheet metal or the like. The bar 50 is connected to the lower end of a cable 51, which is disposed equally between the cables 48 in the case that the center of gravity of the headgear is intermediate those cables, or to one side or the other to accommodate for any imbalance that may exist in the apparatus from side to side.

The cable 51 is connected to a conventional negator spring 52 in a housing that may be suspended from any convenient overhead support, such as a ceiling, beam or the like, by a cable 53 connected between the housing of the negator spring 52 and support means suggested as a hook 54. The hook 54 is connected to the ceiling or other overhead support in any convenient manner, not shown.

As schematically indicated in FIG. 4, the negator spring 52 comprises a housing 55 in which there are rotatably mounted a pair of shafts 56 and 57. A drum 58 fixed on the shaft 56 carries a helical coil of thin, flat strip spring metal that in its unstressed state is tightly wound about the drum 58. An end of the spring 59 is connected to a drum 60 fixed on the shaft 57.

The cable 51 is fixed at one end to, and wound about the shaft 57. In response to a force on the cable 51 great enough to overcome the force required to rotate the drum 60 against the force exerted by the spring 59, the drum 60 will rotate counterclockwise as seen in FIG. 4, drawing more of the spring 59 onto the drum 60 against the force tending to urge it down into a helical coil on the drum 58. With the cable 53 connected to the hook 54 as shown, a constant force on the cable 51 downward in FIG. 2 is required to hold the cable 51 in any extended position over a relatively large range of movement of the cable 51 on and off its coil about the shaft 57. The strength of the spring 59 is selected to support most, but not all of the weight of the headgear 3, leaving a small amount of weight, such as a pound or so, to be supported by the head of the user. By this arrangement, the user can move his head up or down and in any direction, with six degrees of freedom, and the headgear will follow his head movements because of the portion of its weight that is not supported by the negator spring 52. The cable suspension comprising the cables 48 and 51 in the intermediate bar 50 allows this universal movement. It is not preferred to eliminate all of the weight of the headgear 3 in this manner, as that would require a chin strap to move the headgear with the operator when he lowered his head.

As indicated in FIG. 2, the user wearing the headgear 3 observes the patient's eye through a hand lens 60, which may, for example, have a focal length of 2 inches and an aperture of F/1. The lens 60 is shown provided with a handle 61, connected to the lens 60 by means of a frame 62, but if desired the lens 60 may simply be grasped between the fingers of the user.

Figure 6:
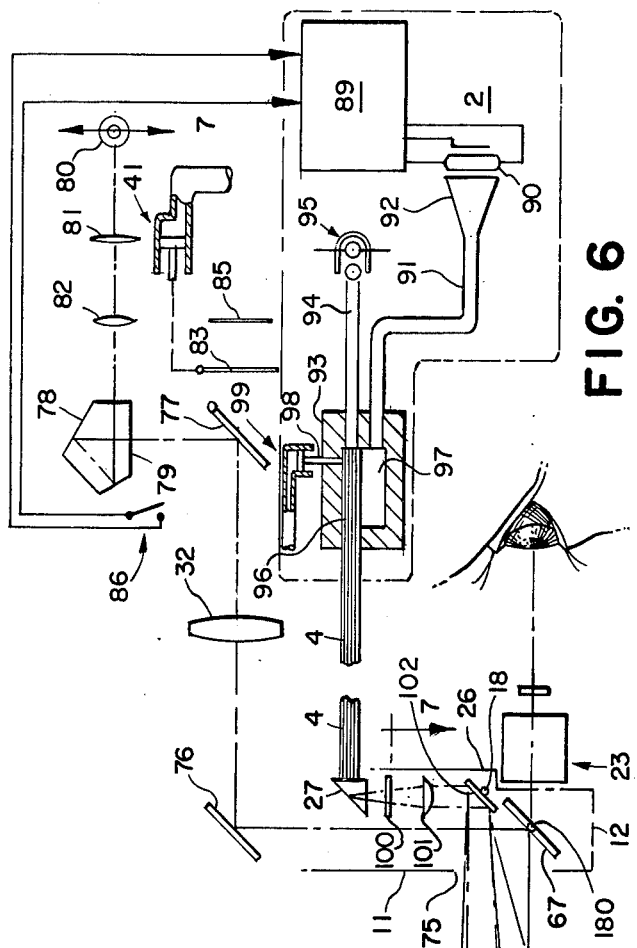
FIG. 6 is a fragmentary schematic elevational sketch, with parts omitted and parts broken away, showing the optical and electrical relationships between the elements of the apparatus of the invention.
Figure 7:
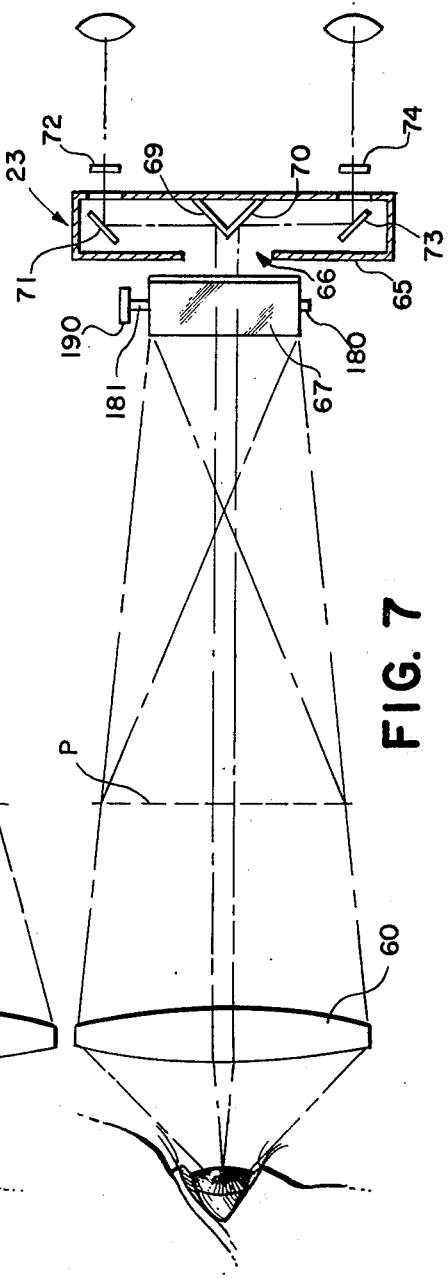
FIG. 7 is a diagrammatic fragmentary top view of a portion of the apparatus of FIG. 6, taken substantially along the lines 7–7 in FIG. 6.

The optical and electrical apparatus of the invention will next be further described with reference to FIGS. 2, 3, 6 and 7. As indicated in FIGS. 6 and 7, the hand lens forms an image of the retina of the patient's eye at a position suggested by the dashed line P. An image of the pupil of the eye is formed in the binocular periscope 23. Referring to FIGS. 6 and 7, the periscope 23 is provided with a housing 65 having an entrance opening 66 facing the hand lens 60, and exposed through a window 75 in the housing 11, as shown in FIGS. 3 and 6.

A beam splitter 67 is mounted on stub shafts 180 and 181 for adjustable rotation under control of a manually operable knob 190 (FIGS. 5 and 7). The beam splitter 67 passes a portion of the light from the image, for example, 20 percent, to the entrance aperture 66 of the periscope housing 65. This light falls on a pair of oppositely inclined mirrors 69 and 70, at right angles to each other and each at 45° to the entering beam.

Light falling on the mirror 69 is reflected to a mirror 71, parallel to the mirror 69, whence it is reflected through an eye lens 73 to the right eye of the examiner. Similarly, light from the mirror 70 is reflected from a mirror 73 and through an eye lens 74 to the left eye of the examiner. The lenses 72 and 74 are preferably of weak positive power, such as one diopter, to allow accommodation of the observer's eye to focus on the image of the retina.

A substantial portion, for example, 80 percent, of the light falling on the beam splitter 67 is directed upwardly through the portion 13 of the housing 11 to fall on a mirror 76 positioned inside the wall 16 of the housing 11 and described above in connection with FIG. 5. Light from the mirror 76 is reflected through the objective lens 32 of the camera to the camera's reflex mirror 77.

As suggested in FIG. 6, the camera is provided with a roof pentaprism 78 on the lower surface 79 of which is formed a focusing screen of any conventional variety, preferably provided with a central area having cross hairs, although a clear circle or a conventional microprism focusing arrangement may be provided if so desired. With the camera in the viewing mode and the mirror 77 in the position shown, the pentaprism 78 is in optical communication with the objective 32 in the optical path described above.

Comparing FIGS. 5 and 6, the illuminator housing 37 contains a lamp 80 energized over the cable 5. A collimating lens 81 is provided to form a beam illuminating the central region of the focusing screen 79 through the eye lens 82 of the camera's viewfinder. In the position of the parts shown, an image of the illuminated zone on the focusing screen 79, and for example, an image of cross hairs on the focusing screen, is formed at the plane P in FIGS. 6 and 7 over a path extending from the focusing screen to the mirror 77, and thence through the lens 32 and to the mirror 76, thence to the mirror 67 and to the imaging plane. When the cross hairs are seen in sharp focus on the image of the retina, through the periscope 23, the camera is in focus. It will be apparent that a portion of the light in the focusing beam will pass through the beam splitter. The inside of the bottom wall 12 of the housing 11 is preferably provided with a black matte surface to inhibit unwanted reflections from this source.

A conventional focal plane shutter for the camera is schematically indicated at 83. As indicated schematically by the dotted line 84, representing any conventional shutter actuating mechanism, the shutter 83 is opened to make an exposure on film located at 85 when the pneumatic actuator 41 is actuated by a pulse of air supplied from the foot unit 1 over the air hose 7.

When the shutter is opened, conventional synchronizing contacts 86 supply a synchronizing signal over the cable 8 to an electronic flash unit indicated in block form at 89 in the energy supply unit 2. The electronic flash unit 89 has as its output device a conventional gas discharge tube 90 with load terminals and a trigger terminal connected to the unit 89. Closure of the camera's synchronizing contacts 86 causes the tube 90 to produce an intense flash of light in a conventional manner. The tube 90 confronts and may be in contact with the end of a fiber optics cable 91. As suggested, the end 92 of the cable 91 may be fanned to conform in shape to the shape of the tube 90, and may be actually engaged with the tube.

The other end of the cable 91 is received in a suitable aperture formed in a light switch housing 93. The housing 93 may be of any conventional opaque material. A second fiber optics cable 94 is connected in the housing 93, and has its opposite end in communication with a conventional projection lamp generally designated 95. Suitable conventional optical elements, such as mirrors and a collimating lens, may be provided to direct light from the lamp 95 primarily into the bundle 94.

One end 96 of the cable 4 extends through a suitable bore in the housing 93 to an enlarged chamber 97 in the housing 93. The actuator arm 98 of a conventional pneumatic actuator 99 extends into contact with the end 96 of the fiber optics cable 4, so that when air is supplied to the actuator 99 over the hose 6, the end 96 of the cable 4 is deflected out of communication with the fiber optics cable 94 and into optical communication with the fiber optics cable 91. The cable 4 thus normally supplies illuminating light to the headgear 3 from the projection lamp 95, and when a photograph is to be made and the actuator 99 is actuated, light is supplied to the cable 4 from the flash tube 90.

As shown in FIG 6, the other end of the cable 4 is against the face of the prism 27. Light from the prism 27 is reflected through any desired conventional filter or filters, as schematically shown at 100, and thence to a collimating lens 101 that forms a narrowly diverging beam. This beam is reflected from an adjustable mirror 102 in the illuminator housing 26 and out through the window 75 to illuminate the image of the retina formed at P.

Figure 8:
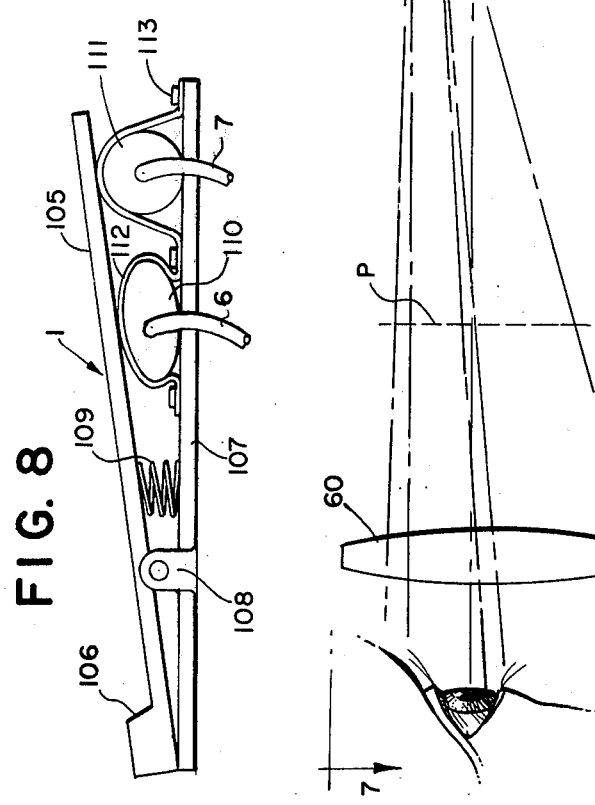
FIG. 8 is a schematic elevational sketch, with parts omitted and parts broken away, of a foot control apparatus forming a part of the system of FIG. 1.

FIG. 8 shows the elements of the foot actuated control unit 1. A foot plate 105 with a heel rest 106 is hinged to a base plate 107 as suggested at 108. A spring 109 normally urges the foot plate 105 to the position shown. A first air bulb 110, connected to the air hose 6, and a second air bulb 111, connected to the air hose 7, are retained on the base plate 107 by means shown as a flexible strap 112 over the air bulbs 110 and 111 and secured to the floor plate 107 by any conventional fasteners suggested at 113. As indicated in FIG. 8, the bulb 110 is precompressed to actuate the light switch actuator 99 before the bulb 111 is compressed sufficiently to actuate the shutter actuator 41. The light switch connections are thus made to communicate with the flash tube 90 just before the shutter is tripped to make an exposure.

Operation of the apparatus of the invention will be generally apparent from the above description. Briefly, referring to FIGS. 2 and 5, the user of the apparatus adjusts the mirror 102 in the illuminator housing 26, with the knob 19 in FIG. 5, until the bright area of light produced by the illuminator is correctly positioned relative to the image of the retina observed through the lens 60. The operator then moves his head until the cross hairs on the focusing screen 79 in FIG. 6 are sharply imaged in superposition on the image of the retina as seen through the periscope 23.

A photograph may be taken by depressing the foot pedal 105, first causing the light switch to be actuated to switch the end 96 of the cable 4 into communication with the cable 91, and then actuating the shutter by means of the pneumatic actuator 41 to begin an exposure. When the shutter is open, closure of the contacts 86 will trigger the flash tube 90, causing a photograph to be taken. Release of the foot pedal will cause the light switch to resume illumination of the subject from the projection lamp 95.

It will be apparent that, if desired, the camera 31 could be mounted over the vertical section 13 of the housing 11, with its lens 32 in the section 13. That would allow the balance of the housing, and the mirror 76, to be omitted. The position of the parts shown was chosen to better balance the headgear. However, it was found in practice that the universal partial suspension is so effective that static balance of the headgear is not necessary.

Film advance may be accomplished manually in the conventional manner, a conventional film advance motor may be provided, or an additional pneumatic actuator, or a solenoid, for example, can be provided for film advance. A motion picture camera may be employed, in which case a bright continuous light source would replace the electronic flash unit.

While the invention has been described with reference to the details of a particular embodiment, many changes and variations will occur to those skilled in the art upon reading this description. Such may obviously be made without departing from the scope of the invention.

Having thus described the invention, what is claimed is:

1. Apparatus for retinal photography, comprising headgear, said headgear comprising a helmet adapted to be worn on the head of the photographer, an indirect opthalmoscope mounted on said helmet, a camera mounted on said helmet, means for optically coupling said camera to said ophthalmoscope to photograph a region of the field seen through said ophthalmoscope, and suspension means for partially suspending said headgear from an overhead support for universal movement in response to a force exerted by the photographer equal to a minor portion of the weight of said headgear.

2. The apparatus of claim 1, in which said optical coupling means comprises a beam splitter mounted on said helmet in the field of view of said ophthalmoscope.

3. Apparatus for retinal photography, comprising headgear, said headgear comprising a helmet adapted to be worn on the head of the photographer, an indirect ophthalmoscope mounted on said helmet, a camera mounted on said helmet, means for optically coupling said camera to said ophthalmoscope to photograph a region of the field seen through said ophthalmoscope, and suspension means for partially suspending said headgear from an overhead support for universal movement in response to a force exerted by the photographer equal to a minor portion of the weight of said headgear, said suspension means comprising spring means adapted to be connected to an overhead support for exerting force equal to a major portion of the weight of said headgear, and flexible cables connected between spaced points on said headgear along a line through the center of gravity of said headgear and said spring means.

4. Apparatus for retinal photography, comprising headgear, said headgear comprising a helmet adapted to be worn on the head of the photographer, an indirect ophthalmoscope mounted on said helmet, a camera mounted on said helmet, means for optically coupling said camera to said ophthalmoscope to photograph a region of the field seen through said ophthalmoscope, and suspension means for partially suspending said headgear from an overhead support, said suspension means comprising means on said headgear forming first and second arms extending from said helmet in opposite directions along an axis through the center of gravity of said headgear, an elongated third arm, first and second cables, said first cable being connected between said first arm and a first end of said third arm, said second cable being connected between said second arm and a second end of said third arm spaced from said first end of said third arm, and negator spring means adapted to be connected to a overhead support and having an output cable extensible over a substantial range in response to a constant force less than the weight of said headgear, said output cable being connected to said third arm at a point between said spaced ends of said third arm.

5. Apparatus for retinal photography, comprising headgear, an energy supply unit, a foot-operated control unit, and suspension means for partially suspending said headgear from an overhead support, said headgear comprising a helmet adapted to be worn on the head of the photographer, an indirect ophthalmoscope mounted on said helmet, a camera mounted on said helmet, said camera having a shutter operable to make an exposure, and means for optically coupling said camera to said ophthalmoscope to photograph a region of the field seen through said ophthalmoscope when said shutter is operated, said suspension means comprising negator spring means adapted to be connected to an overhead support and having an output cable extensible over a substantial range in response to a force slightly less than the weight of said headgear, a bar conneced intermediate its ends to said output cable, and a pair of cables connecting the ends of said bar to spaced points on said headgear along a line through the center of gravity of said headgear, said energy supply unit comprising a first source of light, a second source of light, a first flexible fiber optics cable coupled to said first source of light, a second flexible fiber optics cable coupled to said second source of light, a third flexible fiber optics cable having one end normally coupled to said first source of light, light switch means operable to couple said end of said third fiber optics cable to said second fiber optics cable, means connecting a second end of said third fiber optics cable to said indirect ophthalmoscope to supply illuminating light to said ophthalmoscope, light switch control means responsive to the operation of said foot operated unit for operating said light switch means to couple said third fiber optics cable to said second light source, and shutter control means responsive to the operation of said foot operated unit for operating said shutter.

6. The apparatus of claim 5, in which said second light source is a triggerable electronic flash unit, and further comprising synchronizing means actuated when said shutter is operated for triggering said flash unit.

7. Apparatus for selectively supplying light from a first source and a second source to an ophthalmoscope illuminator, comprising a first flexible fiber optics cable having a first end connected to the illuminator and a second end, a second fiber optics cable having a first end coupled to said first source and a second end, a third fiber optics cable having one end coupled to said second source and a second end, support means mounting said second ends of said second and third cables in adjacent positions, said support means comprising means connected to said first cable near its second end with its second end optically coupled to said second end of said second cable, and actuating means mounted on said support means and operable to bend said second end of said first cable into optical coupling relationship with said second end of said third cable.

8. Apparatus for retinal photography, comprising headgear, said headgear comprising a helmet adapted to be worn on the head of the photographer, an indirect ophthalmoscope mounted on said helmet, a camera mounted on said helmet, means for optically coupling said camera to said ophthalmoscope to photograph a region of the field seen through said ophthalmoscope, and suspension means for partially suspending said headgear from an overhead support, said suspension means comprising negator spring means adapted to be connected to an overhead support and having an output cable extensible over a substantial range in response to a force slightly less than the weight of said headgear, a bar connected intermediate its ends to said output cable, and a pair of cables connecting the ends of said bar to spaced points on said headgear along a line through the center of gravity of said headgear.

9. Apparatus for retinal photography, comprising headgear, said headgear comprising a helmet adapted to be worn on the head of the photographer, an indirect ophthalmoscope mounted on said helmet, a camera mounted on said helmet, means for optically coupling said camera to said ophthalmoscope to photograph a region of the field seen through said ophthalmoscope, and suspension means for partially suspending said headgear from an overhead support for universal movement in response to a force exerted by the photographer equal to a minor portion of the weight of said headgear, said suspension means comprising spring means adapted to be connected to an overhead support for exerting a force equal to a major portion of the weight of said headgear, and flexible cables connected between spaced points on said headgear along a line through the center of gravity of said headgear and said spring means, said spring means comprising a negator spring having an output cable extensible over a substantial distance under a constant force.

* * * * *